US00PP14949P2

(12) United States Plant Patent
Bergman

(10) Patent No.: US PP14,949 P2
(45) Date of Patent: Jun. 29, 2004

(54) CHRYSANTHEMUM PLANT NAMED 'YONORWICH'

(50) Latin Name: *Chrysanthemum×morifolium*
Varietal Denomination: Yonorwich

(75) Inventor: Wendy R. Bergman, Lehigh Acres, FL (US)

(73) Assignee: Yoder Brothers, Inc, Barberton, OH (US)

( * ) Notice: Subject to any disclaimer, the term of this patent is extended or adjusted under 35 U.S.C. 154(b) by 0 days.

(21) Appl. No.: 10/676,792

(22) Filed: Oct. 1, 2003

(51) Int. Cl.[7] ..... A01H 5/00

(52) U.S. Cl. ..... Plt./293

(58) Field of Search ..... Plt./293

*Primary Examiner*—Anne Marie Grunberg
*Assistant Examiner*—Annette H Para
(74) *Attorney, Agent, or Firm*—C. A. Whealy

(57) ABSTRACT

A distinct cultivar of Chrysanthemum plant named 'Yonorwich', characterized by its uniform and outwardly spreading plant habit; strong and freely branching growth habit; dark green-colored foliage; uniform flowering response and habit; early flowering habit; decorative-type inflorescences; red-colored ray florets; and good postproduction longevity with plants maintaining good substance and color for about four to five weeks in an interior environment.

2 Drawing Sheets

Botanical classification/cultivar designation: *Chrysanthemum×morifolium* cultivar Yonorwich.

BACKGROUND OF THE INVENTION

The present Invention relates to a new and distinct cultivar of Chrysanthemum plant, botanically known as *Chrysanthemum×morifolium* and hereinafter referred to by the name 'Yonorwich'.

The new Chrysanthemum is a product of a planned breeding program conducted by the Inventor in Salinas, Calif. and Fort Myers, Fla. The objective of the breeding program is to create new potted Chrysanthemum cultivars that are suitable for year-round production with uniform plant growth habit, good vigor and strong branching habit, numerous inflorescences, desirable inflorescence form and floret colors, fast and uniform flowering response, and good postproduction longevity.

The new Chrysanthemum originated from a cross-pollination made by the Inventor in January, 1999, in Salinas, Calif., of a proprietary Chrysanthemum seedling selection identified as code number YB-4637, not patented, as the female, or seed, parent with a proprietary Chrysanthemum seedling selection identified as code number YB-6489, not patented, as the male, or pollen, parent. The new Chrysanthemum was discovered and selected by the Inventor in November, 1999, as a single flowering plant within the progeny of the stated cross-pollination grown in a controlled environment in Fort Myers, Fla. The selection of this plant was based on its uniform plant growth habit, good vigor and strong branching habit, numerous inflorescences, desirable inflorescence form and floret colors, fast and uniform flowering response, and good postproduction longevity.

Asexual reproduction of the new Chrysanthemum by vegetative tip cuttings was first conducted in Fort Myers, Fla. in February, 2000. Asexual reproduction by cuttings has shown that the unique features of this new Chrysanthemum are stable and reproduced true to type in successive generations.

SUMMARY OF THE INVENTION

The cultivar Yonorwich has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yonorwich'. These characteristics in combination distinguish 'Yonorwich' as a new and distinct Chrysanthemum:

1. Uniform and outwardly spreading plant habit.
2. Strong and freely branching growth habit.
3. Dark green-colored foliage.
4. Uniform flowering response and habit.
5. Early flowering, eight-week response time.
6. Decorative-type inforescences.
7. Red-colored ray florets.
8. Good postproduction longevity with plants maintaining good substance and color for about four to five weeks in an interior environment.

Plants of the new Chrysanthemum differ primarily from plants of the female parent selection primarily in ray floret color as plants of the female parent selection have orange-colored ray florets.

Plants of the new Chrysanthemum differ primarily from plants of the male parent selection in the following characteristics:

1. Plants of the new Chrysanthemum flower about one week earlier than plants of the male parent selection.
2. Plants of the new Chrysanthemum have decorative inflorescences whereas plants of the male parent selection have semi-double inflorescences.

Plants of the new Chrysanthemum can be compared to plants of the cultivar Red Delano, disclosed in U.S. Plant Pat. No. 8,345. In side-by-side comparisons conducted in Fort Myers, Fla., plants of the new Chrysanthemum differed from plants of the cultivar Red Delano in the following characteristics:

1. Plants of the new Chrysanthemum were not as vigorous as plants of the cultivar Red Delano.
2. Plant habit of the new Chrysanthemum was more uniform than plant habit of plants of the cultivar Red Delano.
3. Plants of the new Chrysanthemum flowered about three to four days earlier than plants of the cultivar Red Delano.
4. Ray florets of plants of the new Chrysanthemum were lighter red in color than ray florets of plants of the cultivar Red Delano.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of typical flowering plants of 'Yonorwich'.

The photograph on the second sheet comprises a close-up view of typical inflorescences of 'Yonorwich'.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the spring in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of the pinch, the photoinductive short day/long night treatments were initiated. Plants used for the photographs and description were grown as disbud-types. Measurements and numerical values represent averages of typical flowering plants.

Botanical classification: *Chrysanthemum×morifolium* cultivar Yonorwich.

Commercial classification: Decorative-type potted Chrysanthemum.

Parentage:

*Female, or seed, parent.*—Proprietary *Chrysanthemum×morifolium* seedling selection identified as code number YB-4637, not patented.

*Male, or pollen, parent.*—Proprietary *Chrysanthemum×morifolium* seedling selection identified as code number YB-6489, not patented.

Propagation:

*Type.*—Terminal tip cuttings.

*Time to initiate roots.*—About four days at 21° C.

*Time to produce a rooted cutting.*—About ten days at 21° C.

*Root description*—White, close to 155D; fibrous.

*Rooting habit.*—Freely branching.

Plant description:

*Appearance.*—Herbaceous decorative-type potted Chrysanthemum that is typically grown as a disbud-type. Uniform with lateral branches outwardly spreading; uniformly mounded crown. Strong and freely branching growth habit; about four lateral branches developed after removal of terminal apex (pinching); dense and full plants.

*Plant height.*—About 22.5 cm.

*Plant width.*—About 34 cm.

*Lateral branches* (*peduncles*).—Length: About 15 cm. Diameter: About 4 mm. Internode length: About 1 cm. Strength: Strong. Texture: Pubescent. Color: Close to 144A.

*Foliage description.*—Arrangement: Alternate; simple. Length: About 7.5 cm. Width: About 5.2 cm. Apex: Mucronate. Base: Attenuate to truncate. Margin: Palmately lobed, sinuses between lateral lobes parallel to convergent. Texture, upper and lower surfaces: Pubescent. Color: Developing expanded foliage, upper surface: More green than 147A. Developing expanded foliage, lower surface: More green than 147B. Fully expanded foliage, upper surface: More green than 147A. Fully expanded foliage, lower surface: Close to 147B. Venation, upper surface: Close to 147A. Venation, lower surface: Close to 146A. Petiole length; About 1.9 cm. Petiole diameter: About 3.5 mm. Petiole color, upper surface: Close to 146A. Petiole color, lower surface: Close to 146B.

Inflorescence description:

*Appearance.*—Decorative-type inflorescence form with elongated oblong-shaped ray florets. Inflorescences borne on terminals above foliage. Disk and ray florets develop acropetally on a capitulum. Inflorescences not fragrant. Plants are typically grown as disbud-types.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for about four to five weeks in an interior environment.

*Quantity of inflorescences.*—Grown as a disbud-type, only one inflorescence develops per lateral branch.

*Inflorescence bud.*—Height: About 8 mm. Diameter: About 1 cm. Shape: Oblate. Color: Close to 146A.

*Inflorescence diameter.*—About 8 cm.

*Inflorescence depth* (*height*).—About 3 cm.

*Diameter of disc.*—No disc florets observed.

*Receptacle diameter.*—About 7 mm.

*Ray florets.*—Shape: Elongated oblong. Orientation: Initially upright, then perpendicular to the peduncle and eventually reflexing. Aspect: Incurved to flat to arching. Length: About 4 cm. Corolla tube length: About 3.5 mm. Width: About 9 mm. Apex: Acute to emarginate. Base: Fused into a corolla tube. Margin: Entire. Texture: Smooth, glabrous, satiny. Number of ray florets per inflorescence: About 177 arranged in numerous whorls. Color: When opening, upper and lower surfaces: 9B overlain with 59A. Fully opened, upper surface: 9B overlain with 53A to 59A. Fully opened, lower surface: 9D underlain with 59A.

*Disc florets.*—No disc florets observed.

*Phyllaries.*—Quantity per inflorescence: About 23. Length: About 8 mm. Width: About 3 mm. Shape: Deltoid. Apex: Acute. Base: Truncate. Margin: Entire. Texture, upper surface: Waxy, smooth. Texture, lower surface: Pubescent. Color, upper surface: Closest to 146A. Color, lower surface: Close to 144A to 146A.

*Reproductive organs.*—Androecium: None observed. Gynoecium: Present on ray florets. Style color: Close to 144B to 144C. Stigma color: Close to 9A.

*Seed/fruit.*—Seed and fruit production has not been observed.

Disease/pest resistance: Resistance to pathogens and pests common to Chrysanthemums has not been observed on plants grown under commercial greenhouse conditions.

It is claimed:

1. A new and distinct cultivar of Chrysanthemum plant named 'Yonorwich', as illustrated and described.

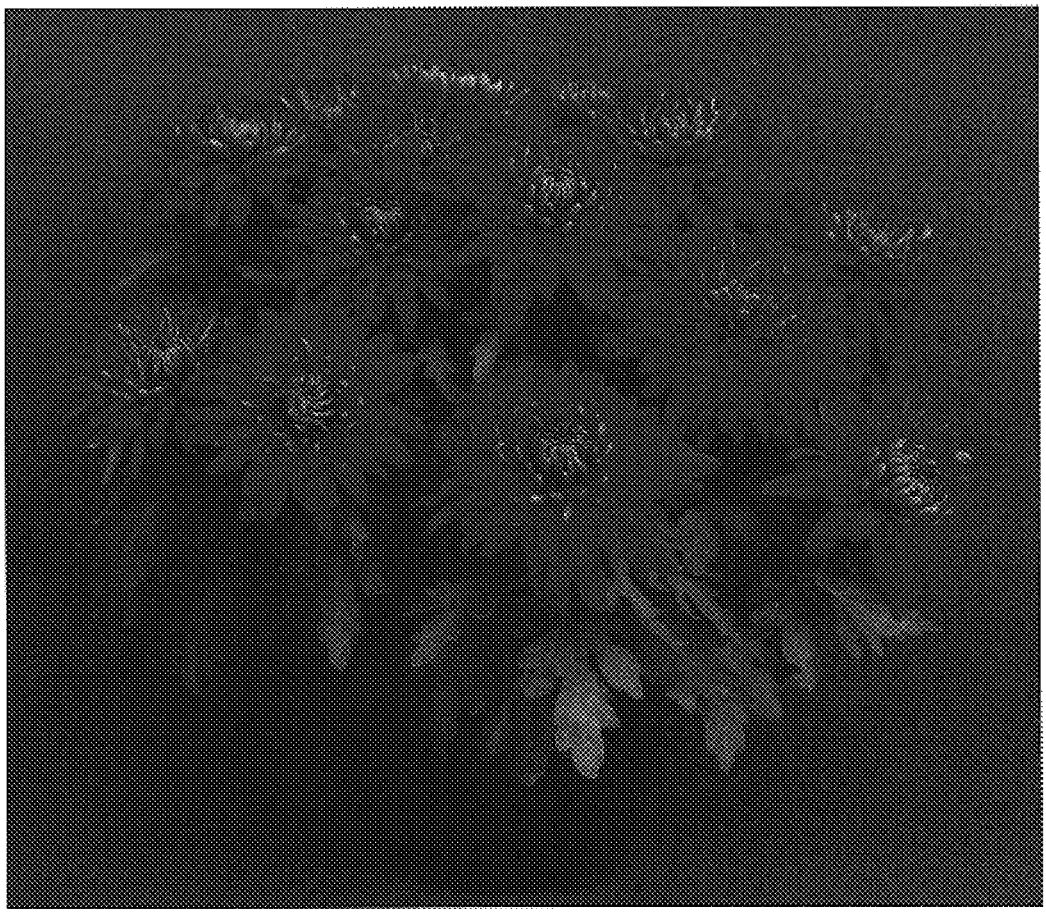

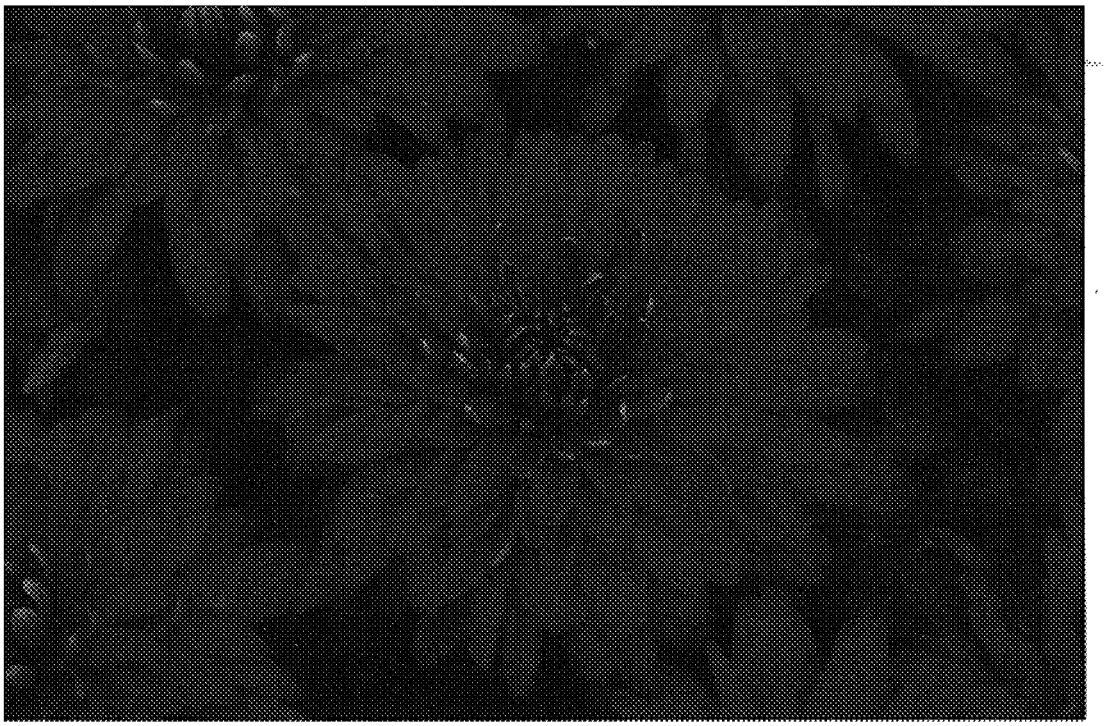

* * * * *